United States Patent [19]

Rolle

[11] 4,045,676

[45] Aug. 30, 1977

[54] DETERMINING ELEMENT CONCENTRATIONS IN SAMPLES

[75] Inventor: Rainer Rolle, Randburg, Transvaal, South Africa

[73] Assignee: Ortec Incorporated, Oak Ridge, Tenn.

[21] Appl. No.: 558,190

[22] Filed: Mar. 13, 1975

[30] Foreign Application Priority Data

Mar. 15, 1974 South Africa .................. 74/1707

[51] Int. Cl.$^2$ .................................. G01N 23/20
[52] U.S. Cl. ........................ 250/272; 250/273
[58] Field of Search ............ 250/458, 459, 460, 253, 250/272, 273, 255

[56] References Cited

U.S. PATENT DOCUMENTS

| 2,407,938 | 9/1946 | Schonander | 250/458 |
| 2,863,061 | 12/1958 | Destriau | 250/458 |
| 2,990,475 | 6/1961 | Scherbatskoy | 250/253 |

OTHER PUBLICATIONS

*Detection Limit for Gold by Radioisotopic X-Ray Analysis* Burkhalter & Marr, International Journal of Applied Radiation & Isotopes, (pp. 395-403) 1970, vol. 21.

*Some Aspects of X-ray Fluorescence Spectrometers for Trace Element Analysis* Nuclear Instruments and Methods, 101, 1972, (pp. 127-135).

*Primary Examiner*—Craig E. Church
*Attorney, Agent, or Firm*—Kenway & Jenney

[57] ABSTRACT

The invention provides a method and apparatus for determining the concentration of an element such as a heavy metal in a matrix of a material such as rock by the X-ray or gamma-ray fluorescence technique.

It allows the use of this technique where a sample to be analyzed has a rough or jagged surface. The effect of the rough surface is eliminated by adjusting the distance between the source and/or detector from the sample so that the rate of detection of radiation in a reference energy band is maintained constant for all samples, including reference samples used for calibration. The reference band is at least partly outside the band or bands characteristic of the element sought.

26 Claims, 4 Drawing Figures

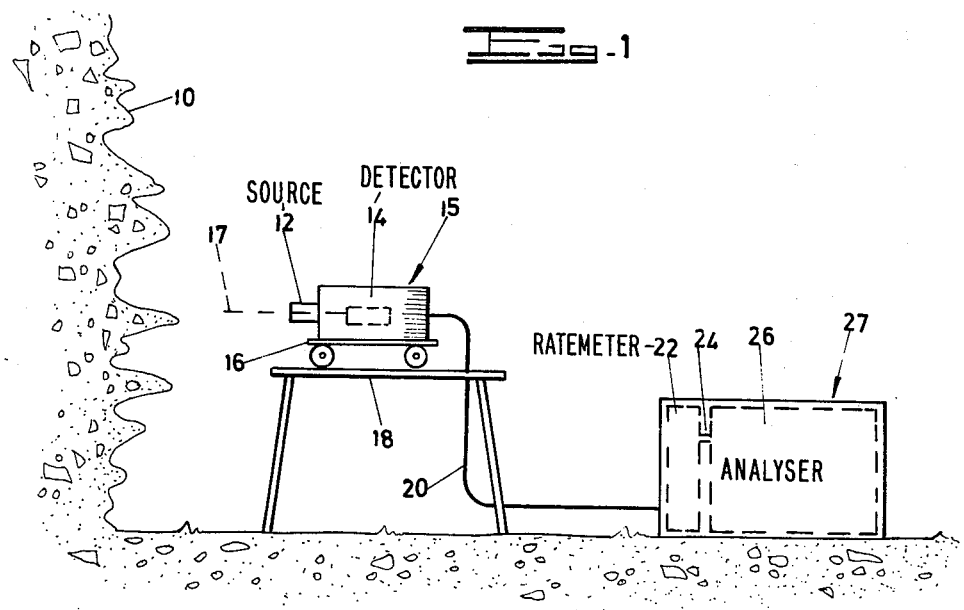
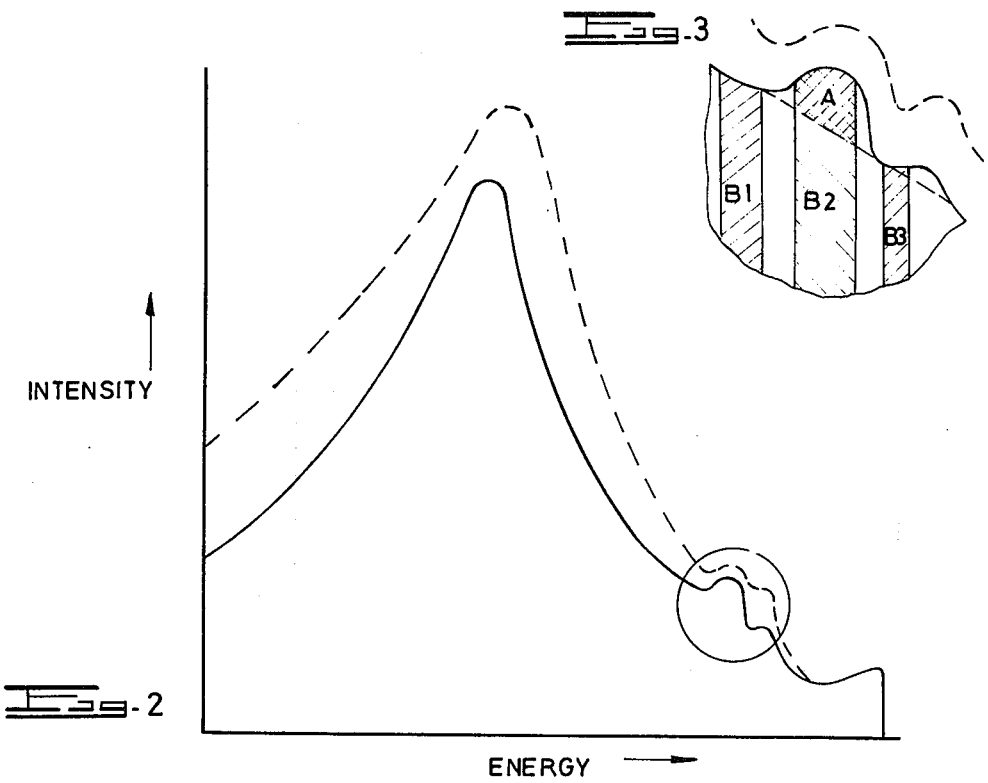

DETERMINING ELEMENT CONCENTRATIONS IN SAMPLES

The invention has particular application in sampling in situ in mines

This invention relates to the determination of concentrations of elements such as heavy metals in materials such as ore samples using the technique of X-ray or gamma-ray fluorescence.

The basic principles of this technique are well known. The atoms of all elements can be excited to give off one or more X-rays, and the energies of those X-rays are characteristic of the element giving them off. In fluorescence techniques X-rays or gamma-rays of energies higher than those of the characteristic X-rays of an element are used to excite the atoms of the element.

If the high energy X-rays used for excitation are shone upon a sample, and the X-rays which are emitted by the sample are detected and analysed into various energies, it is found that there is a broad band of scattered X-rays in energies less than those of the exciting source, which make up a continuum background, and there are also peaks due to the excitation of the characteristic X-rays from elements in the sample. The ratio of the intensity of the radiation in any peak to the intensity of the background at the same energy (known as the peak-to-background ratio) is a measure of the concentration of the element which has characteristic X-rays at the energy of that peak.

If the geometrical arrangement of the source of exciting X-rays, the sample and the detector is kept constant, then the peak-to-background ratio has been found to be quantitative (in the sense of indicating the concentration of the element rather than merely indicating the qualitative fact of the identity of the element) and so permits direct determination of the concentration of the element.

This technique has been applied industrially to the analysis of a variety of elements in various matrixes. However, a continuing problem with this type of analysis has been sample preparation, because it has hitherto been thought that the analysis only becomes quantitative (in the sense described above) if the geometrical arrangement of the exciting source, the sample and the detector is fixed. Obviously if the sample is rough relative to the distances between the source and the bulk of the sample and the detector it becomes impossible to define such a fixed geometrical arrangement. In practice this has meant that heretofore there has been no method for analysing rough samples such as broken rock surfaces. This has been particularly true when analysing light elements in lighter matrixes, but it has been found when analysing heavy element in light matrixes it is possible to overcome some of the effects of surface roughness.

For instance, the specific case of determining gold concentrations in ores has been described in an article by Burkhalter and Marr in the *International Journal of Applied Radiation and Isotopes*, 1970, vol. 21, pp 395–402. In this article the general principles of the method of analysis by X-ray fluorescence are clearly described, and the advantage of using high-energy X-rays to excite the K X-rays of gold dispersed in a lighter element matrix are given on page 396 of that article. However, for the procedure described in that article, and all others which describe this type of analysis, it has been necessary to prepare the samples to make the surface which is exposed to the exciting radiation relatively flat.

What I have found is that it is possible to use some or all of the continuum background spectrum to standardise the measurement so that when analysing rough or jagged samples such as the exposed face of an ore body in a typical mine or a pile of broken rock it is possible to arrange the source and detector in a position relative to the sample such that the analysis yields the same peak-to-background ratio as when analysing a smooth sample containing the same concentration of the element of interest. This has permitted the development of a method for analysing elements such as gold in situ on rock faces exposed by mining which are extremely rough and which could not otherwise be analysed by the X-ray fluorescence technique unless an excessive time were taken to make the surface smooth.

The invention proposes a method for determining the concentration of an element in an unknown sample by X-ray fluorescence, in which method at least one calibration sample containing known concentrations of the element of interest is analysed, and during the analysis of the calibration sample the rate is determined at which scatterd radiation is detected over a reference energy range so chosen that most if not all of that range lies outside the energy band in which those fluorescent X-rays of the element of interest lie, which are employed for the analysis of the concentration of the element; and performing an X-ray fluorescence analysis on the unknown sample (which may or may not have a rough surface) by adjusting or varying the position of the source or detector or both relative to the unknown sample until the rate at which the scattered radiation is detected in the reference energy range is the same as it was when the calibration sample was being analysed.

Conventional sources such as those used by Burkhalter and Marr, op.cit., and those used for the purposes of my invention are shielded and emit radiation in a space limited by the shape of the shield. In one common case the shield is flat the space is generally hemispherical or conical or even, in a limiting case where the shield is tubular and the source is set deeply in it, the space is cylindrical. In all practical cases however the space in which radiation is emitted by a shielded source has an axis, and the expression "axis of the source" used in this specification has the meaning described in this paragraph. Likewise, radiation detectors detect radiation in a space having an axis, which axis is in tended by the term "axis of the detector" in this specification.

In one version of the geometrical conditions or arrangements of my invention, two or more calibration samples each with a smooth prepared surface are used and the measurements are carried out by irradiating those surfaces of the samples in sequence. The radiation source and detector are spaced a relatively short fixed distance apart with their axes aligned and both being spaced a relatively large distance from the flat surface of the sample on a line substantially normal to that surface. A reference value of the detected radiation in a selected radiation range is established for the first sample, and when subsequent samples are investigated they are moved along the common axis until the rate of detected radiation coincides with the reference value. When a rough-surfaced sample is to be analysed, it need merely be placed at some point along the common axis and moved in any direction relatively to the source and detector until the detected radiation rate equals the reference value.

In an alternative version, the samples are kept in a fixed position and the source and detector, again arranged coaxially, are moved relatively to each other along their common axis until the measured rate of detected radiation is equal to a reference value established when the first sample was irradiated.

If one or more of the reference samples is or are rough-surfaced — and in theory all may be — it is merely necessary to establish for any one of the reference samples (smooth-surfaced or rough-surfaced) a reference value in the reference energy range, and to vary the distance of the other samples relatively to the source and detector or relatively to both by movement along their common axis in order to equalise the measured rate of detected radiation in that range with the reference value.

The reference energy range should be as wide as possible. In many cases of interest, particularly in analysing rock samples to determine the concentration of elements that occur in concentrations of the order of parts per million, the excited characteristic radiation is only a negligible part of the total quantity of detectable radiation in a wide energy range, and it is possible to include the whole of the characteristic band in the reference range.

The samples should all be of comparable size and preferably of effectively infinite size in the sense described by Burkhalter and Marr, op.cit., at page 398, that is samples which have sufficient surface area and depth when seen by the detector to yeild an intensity of radiation in the energy bands of interest which is greater than 95 percent of the intensity yielded by a sample of infinite area and thickness.

Apparatus according to the invention comprises a radiation source, a radiation detector, means to support the source and detector in predetermined positions relatively to a sample to be irradiated by the source, analyser means for sorting radiation detected by the detector into one or more energy bands and measuring its intensity, and analogue means to indicate the rate of detection of radiation by the detector.

In a preferred form the analogue means is a radiation ratemeter. Alternatively it could be a flashing light device or an audio device or the like.

The analyser means will normally be a multi-channel analyser for measurements of the detected radiation in the characteristic band and any other bands necessary to compute the value of the characteristic radiation as distinct from the scattered or background radiation.

In practice it is desirable, particularly for in situ mineral analysis, for the source and detector to be mounted in a first housing which is connected by a flexible cable to a second housing in which the analyser means is accommodated. At least the first housing may be adapted to be hand-held for the in situ analysis.

Where the apparatus is too bulky to be conveniently hand-held for in situ investigations, it is convenient for the housing containing the source and detector to be mounted on a stand or frame which is adapted to be set up at a fixed station relatively to the rock face, the housing being guided for relative movement on the stand so that the distance of the source and detector from the face can be easily adjusted.

The source and detector may be mounted a fixed distance apart in the first housing; or they may be coaxial and movable relatively to each other along the common axis.

The source used will normally be a radioisotope. It is convenient to shield it in the conventional way so that it emits radiation in a generally conical space and to mount it coaxially with a detector which also has an axis as described earlier. When the apparatus is used on any flat-surfaced sample, it is convenient to orientate the coaxial source and detector normally to that surface.

IN THE DRAWINGS

FIG. 1 is a semi-schematic representation of typical apparatus for carrying out the invention, seen in use for analysing mineral values in situ underground in a mine;

FIG. 2 is a simplified typical curve of the intensity of detected radiation plotted against energy of irradiation; and FIG. 3 is an enlarged version of the portion of the curve circled in FIG. 2, certain energy bands of interest being indicated;

Figure 4:
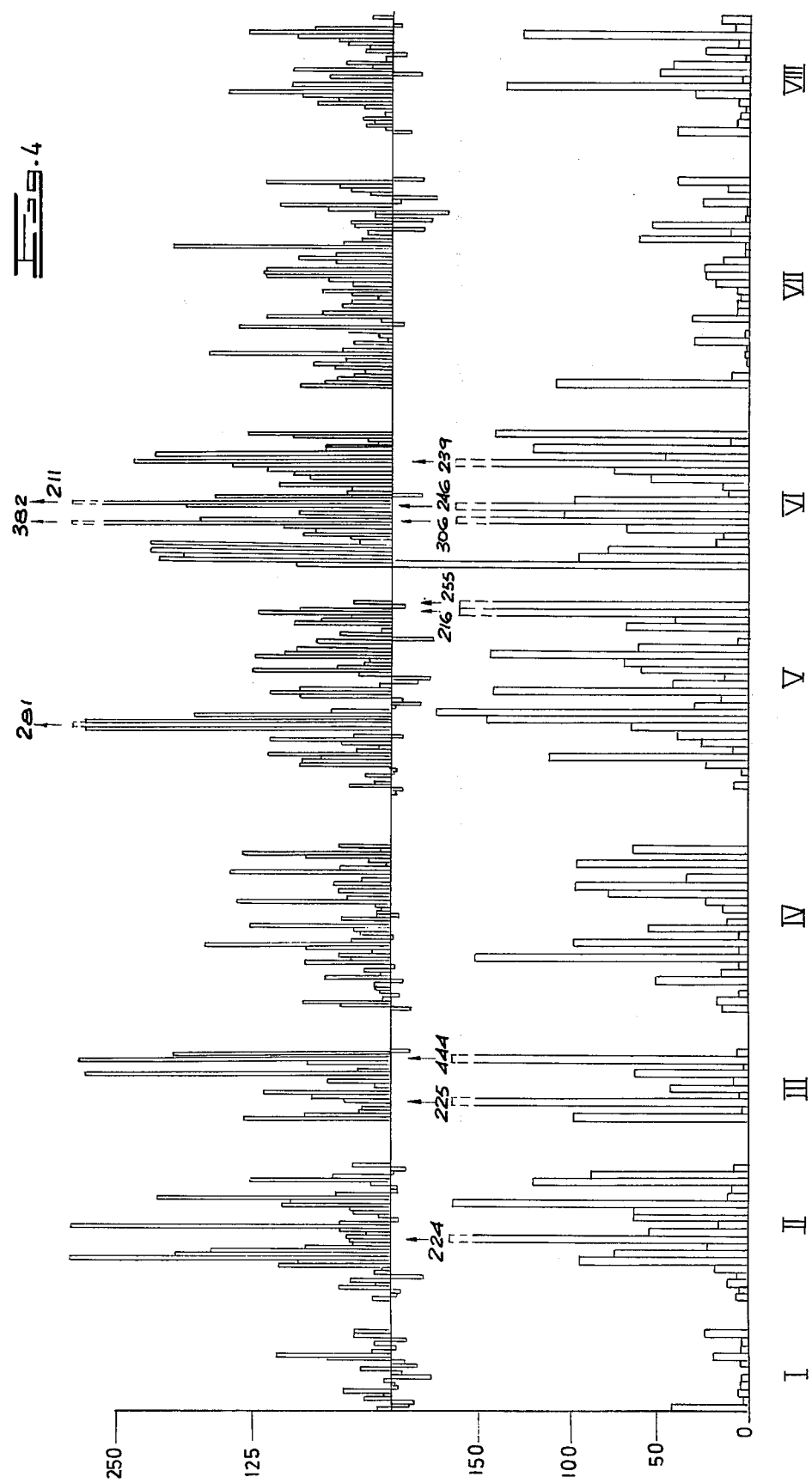
Figure 5:
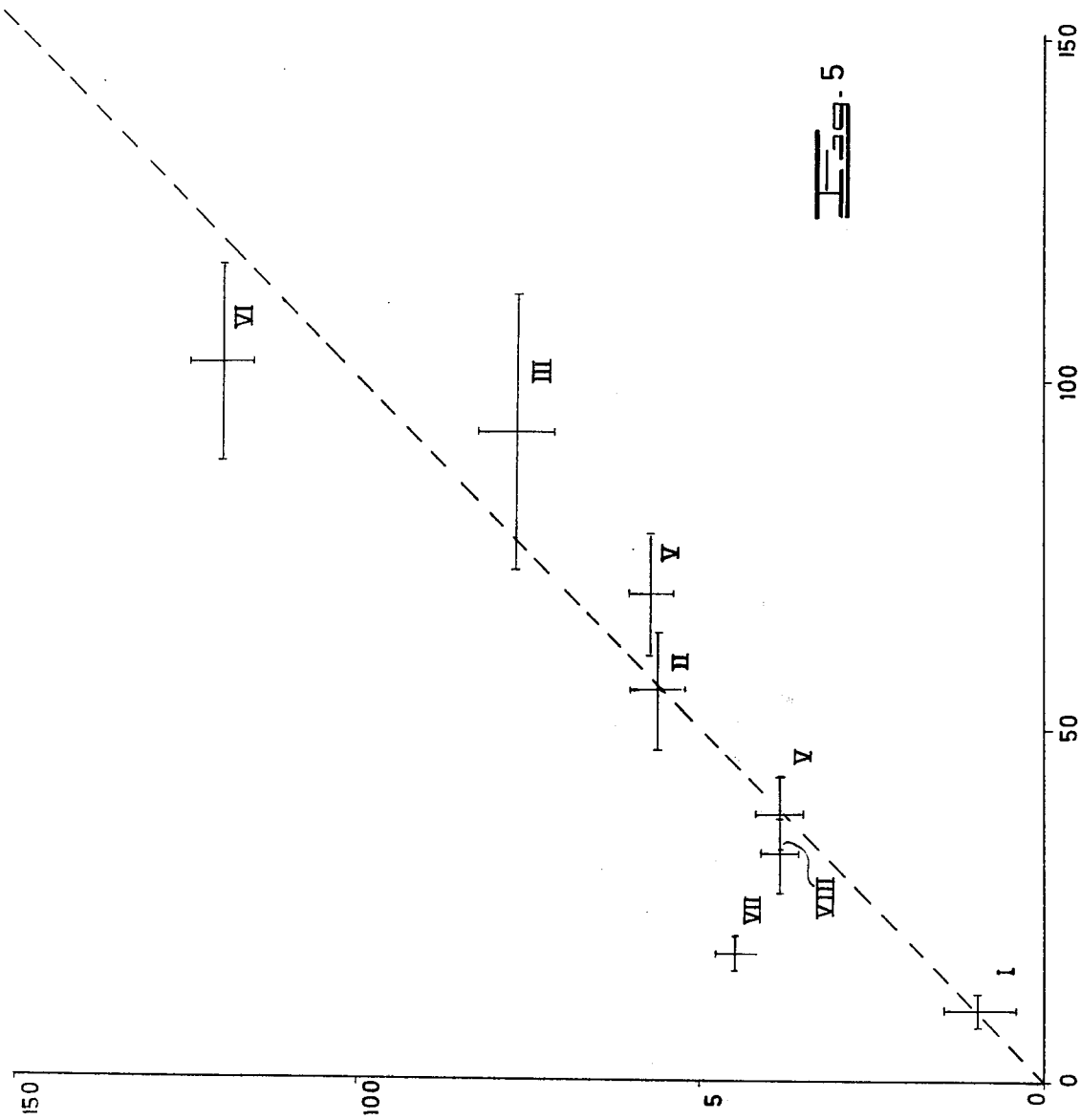

FIG. 4 is a graphical representation of the results obtained by the method and apparatus of the invention (in the upper part of the figure) in gold sampling on a South African mine as compared with the results of conventional sampling (lower part). In both parts, groups of individual samples are represented on the horizontal axis by Roman numerals and the gold content is represented in parts per million on the vertical axis; and FIG. 5 is a graphical comparison of the two sets of results illustrated in FIG. 4, standard deviation being indicated. The vertical axis represents the results obtained by the invention and the horizontal axis represents the results by conventional sampling.

In FIG. 1, a rough face 10 of a gold-bearing ore body is irradiated in situ by a source 12 mounted coaxially with and at a fixed distance from a detector 14 in a housing 15 on a first support part of the apparatus in the form of a slide or trolley 16 that is movable in a direction parallel to the common axis 17 of the source and detector on a second support part in the form of a stand 18 set up on the ground in front of the face 10. A flexible cable 20 connects the detector 14 to an analogue device in the form of a ratemeter 22 that is in turn connected by a cable 24 to a multi-channel analyser 26 mounted with the ratemeter in a common housing 27. The source may conveniently be a small radioisotope source shielded so that it emits its radiation in the customary conical space ahead of it. The detector is a solid-state detector cooled by liquid nitrogen. It operates on a conical space ahead of it. The analyser is preferably capable of analysing energy precisely into a number of channels, where the range of each channel is presettable over a wide energy spectrum. The typical form of an energy spectrum as detected by the apparatus of FIG. 1, applied to a gold-bearing sample, is shown in FIGS. 2 and 3. Scattered photons account for the general form of the curve, and the excited radiation from the gold accounts only for the peaks of relatively low intensity seen in the circled area of the curve. One of these peaks, cross-hatched and marked A in FIG. 3, corresponds to the excited characteristic $K_{\beta_1}$ X-rays of gold in the energy band 77.5–78.5 keV.

For a change in geometry of the source and detector arrangements, the observed spectrum changes position, for instance from the solid-line position in FIG. 2 to that shown in dash lines. There is a marked shift in the energy band characteristic of the gold $K_{\beta_1}$ X-rays; hence the importance of standardising the geometry by the system of the invention.

The apparatus described above is suitable for scientific purposes where its bulk is not of particular relevance. For use as a mining tool in sampling and in verifying that mining is taking place on reef, it is desirable that at least the first housing should be light enough and otherwise adapted to be hand-held by the operator even when the apparatus is in use. For practical mining purposes the slight relative movements inevitable with hand-held equipment will normally have a negligible effect on the reliability of the analysis results.

The utility of the invention was verified by the procedure described below.

This procedure involved determining by known chemical methods the gold concentration in five powdered siliceous ore samples, and then forming the samples into flat-surfaced bodies and using them as calibration samples to measure, by the X-ray fluoressence technique, the excited characteristic radiation they emitted in a predetermined suitable energy band when irradiated with a source of sufficient power and under standarised conditions of irradiation and detection. To simulate rough-surfaced samples, the surfaces of the same bodies were roughened to create randomly dispersed troughs and protrusions several centimeters in depth and height, and the method of the invention was applied to them.

The gold content of the five samples as determined by chemical analysis was as set out in the second column of the accompanying table.

The source used was a Cd-109 radioisotope of 80 mCi shielded by tungsten sheet and mounted coaxially with a 100mm$^2$ Ge (Li) solidstate detector cooled by liquid nitrogen. The detector was connected to a multichannel analyser for accurate measurements and to a ratemeter for an analogue indication of the rate of emission of radiation in a chosen reference energy range from the samples.

To establish the above-mentioned reference value of the detected radiation in a reference energy range comprising the spectrum between the limits 20 keV and 88 keV, the smooth-faced samples were irradiated with the source placed 4 cm from the sample surface. The integrated rate in this range was found to be approximately 20,000 counts per second (20 kHz), a value constant for all the samples under the standardised geometrical conditions. Each of the samples was roughened and then analysed by placing it in turn before the source and detector and adjusting their position relatively to the sample to give an integrated ratemeter count of 20 kHz. In this position a measurement of the ratio A/B$_2$ was made, and the gold concentration so derived.

This measurement was made by noting the scattered radiation B$_1$ of energy 76–77 keV and that B$_3$ of energy 79–79.3 keV, and interpolating between these to obtain the scattered radiation B$_2$ in the energy band 77.5–78.5 keV, which previous experimentation had shown to be a suitable characteristic band for the K$_{\beta_1}$ fluorescent radiation of gold. The scattered radiation in the bands B$_1$ and B$_3$ was measured to determine the background at the gold peak, B$_2$, according to methods known in the art, and the bands do not represent the reference energy range chosen.

The total intensity A + B$_2$ in the characteristic band 77.5–78.5 keV was measured for each sample and the value of A derived by subtracting the calculated value of B$_2$ from A + B$_2$. (The curve for interpolation between B$_1$ and B$_3$ was found prior to the test described on samples of identical composition but containing no detectable gold).

The results of the test were:

| Sample No. | Gold content (g Au/t) determined chemically | Gold content (g Au/t) determined by the invention | Ratio rough/flat |
|---|---|---|---|
| 1 | 998 | 1,006 | 1.008 ± 0.010* |
| 2 | 348.6 | 350.0 | 1.001 ± 0.010* |
| 3 | 157.0 | 152.9 | 0.974 ± 0.023* |
| 4 | 109.5 | 114.1 | 1,042 ± 0.035* |
| 5 | 66.9 | 69.8 | 1.043 ± 0.050* |
| | | Mean | 1.014 ± 0.030* |

*Standard deviation on measurement.

It is clear from this test that roughness of the sample has no significant effect upon the determination when the invention is applied.

The utility of the invention was further demonstrated in a test on a rough rock surface in situ underground. The instrument was calibrated as described above, and used to determine the gold concentration in the rock face. A series of rectangles 160mm wide by 80mm high was marked along the face, and the gold concentration in each 80mm by 80mm half of each rectangle was determined by the method described previously. Then the rock within each rectangle was chipped out with a hammer and chisel to an approximate depth of 20mm. The chips were collected and taken to surface for determination of the gold content by conventional fire assay methods. Accordingly there were two results by the method of the invention for each single result obtained by chip sampling.

The results of the analyses performed by the two methods are shown in FIG. 4 for eight different areas on the rock face marked in groups from I to VIII. The upper part of FIG. 4 shows the results obtained by the method of the invention, the lower part showing the results obtained by the conventional technique. In both parts the results are given in parts per million. The apparent negative values shown in the upper part of FIG. 4 arise from statistical variations in the number of counts registered in the various channels A, B$_1$, B$_2$, and B$_3$ of FIG. 3.

The same results are compared in FIG. 5, in which the mean values determined for each group I to VIII are shown by the intersection of the crosses, and the lengths of the arms of the crosses are proportional to the standard deviation of the individual group results on either side of the mean value. The results obtained by the system of the invention are plotted on the vertical axis and the results obtained by the conventional technique on the horizontal axis, both in parts per million.

It is clear that the results given by the two methods are in agreement. Analysis of the results by standard statistical methods showed that the method of this invention was more accurate than the chip sampling method, when the same time was taken to do the measurements by each method. Furthermore, these tests demonstrated the feasibility of calibrating the apparatus against a large number of very rough-surfaced samples in which the gold was distributed heterogeneously.

I claim:

1. A method of determining the concentration of an element in a sample which has a rough surface comprising the steps of:
    A. irradiating at least one calibration sample of known concentration of the element to excite rdiation from the element in a known energy band characteristic of the element and
  i. measuring such radiation to establish a relationship between the measured characteristic radiation and the concentration of the element, and
  ii. measuring under substantially the same geometrical conditions of irradiation and detection as in step A.i., the rate of emission of detected radiation in a reference energy range, said reference energy range being relatively wide compared to said characteristic band such that the ratio of the characteristic radiation to reference range radiation is small, such rate establishing a reference value for that range; and
B. irradiating the rough surfaced sample to be analyzed,
  i. first measuring the rate of emission of detected radiation from that sample in said reference energy range, while varying the geometrical conditions of irradiation and detection until the measured rate of detected radiation in the reference energy range is equal to the established reference value, and
  ii. then, under the same geometrical conditions for which said measured rate of detected radiation in the reference energy range equaled said established reference value in step B.i., measuring the excited radiation of that sample in only the characteristic band, and from such measurement and the established relationship, determining the concentration of the element in that sample.

2. The method of claim 1 in which irradiation and detection take place in spaces having a common axis.

3. The method of claim 2 in which the geometrical conditions are varied by maintaining the positions at which irradiation and detection take place a constant distance apart and moving both such positions relatively to the sample along the common axis.

4. The method of claim 2 in which the geometrical conditions are varied by moving the positions at which irradiation and detection take place relatively to each other along the common axis.

5. The method of claim 1 in which the element whose concentration is to be determined is gold and the characteristic energy band is substantially 77.5 to 78.5 keV.

6. The method of claim 1 in which the sample is irradiated by radiation from a Cd - 109 source which is shielded by tungsten sheet.

7. The method of claim 1 in which the samples are effectively of infinitely large size.

8. The method of claim 1 in which the calibration samples has a rough surface.

9. The method of claim 1 in which the element whose concentration is to be determined is gold and the reference energy range is substantially 20 to 88 keV.

10. The method of claim 1 in which the sample to be analysed is part of a rock face and the method is applied in situ.

11. The method of claim 1 in which there are a plurality of calibration samples each having a smooth surface and the measurements on them are carried out by irradiating them in sequence along an axis normal to their smooth surfaces.

12. The method of claim 1 in which the detector is a solid-state detector cooled by liquid nitrogen.

13. The method of claim 12 in which the detector is a germanium detector.

14. A method of determining the concentration of an element in a plurality of samples, some of which have a rough surface comprising the steps of:

A. irradiating at least one calibration sample of known concentration of the element to excite radiation from the element in a known energy band characteristic of the element and
  i. measuring such radiation to establish a relationship between the measured characteristic radiation and the concentration of the element, and
  ii. measuring under substantially the same geometrical conditions of irradiation and detection as in step A.i., the rate of emission of detected radiation in a reference energy range, said reference energy range being relatively wide compared to said characteristic band such that the ratio of the characteristic radiation to reference range radiation is small, such rate establishing a reference value for that range; and
B. irradiating a rough surfaced sample to be analyzed, and
  i. first measuring the rate of emission of detected radiation from that sample in said reference energy range, while varying the geometrical conditions of irradiation and detection until the measured rate of detected radiation in the reference energy range is equal to the established reference value, and
  ii. then, under the same geometrical conditions for which said measured rate of detected radiation in the reference energy range equaled said established reference value in step B.i., measuring the excited radiation of that sample in only the characteristic band, and from such measurement and the established relationship, determining the concentration of the element in that sample.

15. The method of claim 14 in which the element whose concentration is to be determined is gold and the characteristic radiation band is substantially 77.5 to 78.5 keV.

16. The method of claim 14 in which the samples are effectively of infinitely large size.

17. The method of claim 14 in which the calibration sample has a rough surface.

18. The method of claim 14 in which the element whose concentration is to be determined is gold and the reference energy range is substantially 20 to 88 keV.

19. The method of claim 14 in which the sample to be analyzed is part of a rock face and the method is applied in situ.

20. The method of claim 14 in which there are a plurality of calibration samples each having a smooth surface and the measurements on them are carried out by irradiating them in sequence along an axis normal to their smooth surfaces.

21. The method of claim 14 in which the sample is irradiated by radiation from a Cd-109 source which is shielded by tungsten sheet.

22. The method of claim 14 in which the detector is a solid state detector cooled by liquid nitrogen.

23. The method of claim 22 in which the detector is a germanium detector.

24. The method of claim 14 in which irradiation and detection take place in spaces having a common axis.

25. The method of claim 24 in which the geometrical conditions are varied by maintaining the positions at which irradiation and detection take place a constant distance apart and moving both such positions relatively to the sample along the common axis.

26. The method of claim 24 in which the geometrical conditions are varied by moving the positions at which irradiation and detection take place relatively to each other along the common axis.

* * * * *